United States Patent [19]

Shapiro

[11] 4,350,814
[45] Sep. 21, 1982

[54] PYRROLO [3,4-C]QUINOLINE COMPOUNDS

[75] Inventor: Howard S. Shapiro, Wilmington, Del.

[73] Assignee: ICI Americas Inc., Wilmington, Del.

[21] Appl. No.: 223,527

[22] Filed: Jan. 8, 1981

Related U.S. Application Data

[62] Division of Ser. No. 87,458, Oct. 22, 1979, Pat. No. 4,268,513.

[51] Int. Cl.$^3$ .................. C07D 491/14; C07D 491/22
[52] U.S. Cl. ...................................... 546/84; 546/65; 424/258
[58] Field of Search .................... 546/84, 65; 424/258

[56] References Cited

U.S. PATENT DOCUMENTS

3,024,243  3/1962  Sang et al. ......................... 546/113

OTHER PUBLICATIONS

H. Fritz et al., "Cyclisierung von Phenylhydrazonen . . . ," *Liebigs Ann. Chem.*, 762, 121-126, (1972).
J. M. Fayadh et al., "The Chemical Effects of γ-Radiation . . . " *J. Chem. Soc.*, 1781-1784, (1969).
H. Fritz et al., "Eine neue Synthese fur 2H-Pyrrolo . . . ," *Liebigs Ann. Chem.*, 255-265, (1975).
R. B. Roy et al., "Studies on the Reaction of Benzoyl Peroxide . . . ", *J. Chem. Soc.*, 1886-1891, (1969).

*Primary Examiner*—Alan L. Rotman
*Attorney, Agent, or Firm*—David J. Levy; John M. Sheehan

[57] ABSTRACT

Pyrrolo [3,4-c]quinolines are described which have various substitutions at the 2, 4, 5, 6, 7, 8 and 9 positions. The group of compounds has been found to possess unexpected pharmaceutical utilities including antipsychotic, analgesic and antidepressant activities. Also set forth are various methods of making the compounds as well as pharmaceutical compositions containing them.

7 Claims, No Drawings

PYRROLO [3,4-C]QUINOLINE COMPOUNDS

This is a division, of application Ser. No. 87,458, filed Oct. 22, 1979, now U.S. Pat. No. 4,268,513 issued May 19, 1981.

The present invention relates to certain pyrrolo [3,4-c]quinolines and, more specifically, to hexahydropyrrolo [3,4-c]quinolines which demonstrate useful antipsychotic and analgesic properties.

The use of antipsychotic drugs is well known but there is still a need for an antipsychotic agent which is free from extrapyramidal side effects, e.g. tremor, rigidity, facial tics, diskinesias, etc. Consequently, compounds which demonstrate antipsychotic activity and are free from side effects are highly desirable, especially if they are effective in cases of clinical schizophrenia that are refractory to present chemotherapy.

The principal object of the present invention is to provide a group of antipsychotic agents which appear to give a minimum of side effects. It is also an object of the invention to provide compounds which demonstrate useful analgesic activity. Other objects will also be hereinafter evident.

Most of the compounds comtemplated for use herein are new. However, a few of the compounds have been described in the literature but not as antipsychotic or analgesic agents (see in particular Roy et al., J. Chem. Soc. C, 1969, 1886-1891 and Fayadh et al., J. Chem. Soc. C, 1969, 1781).

Broadly stated, the novel compounds of the invention are hexahydropyrrolo [3,4-c]quinolines of the following Formula (I):

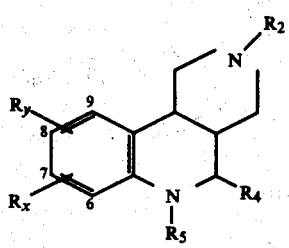

wherein
$R_2$ is hydrogen, $C_1$-$C_6$ normal alkyl,
$C_3$-$C_6$ cycloalkyl, $C_1$-$C_6$ hydroxyalkyl,
$C_3$-$C_6$ hydroxycycloalkyl, phenyl, benzyl,

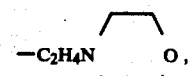

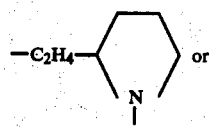

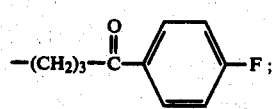

$R_4$ is hydrogen, $C_1$-$C_3$ alkyl or phenyl;

$R_5$ is hydrogen, $C_1$-$C_6$ alkyl, $C_3$-$C_6$ cycloalkyl, acetyl, benzyl or $CH_2CF_3$, or when $R_4$ and $R_5$ are alkyl, they combine to form a 5-, 6- or 7-membered ring; and $R_x$ and $R_y$, which may be the same or different, are hydrogen, halogen, trifluoromethyl, $C_1$-$C_6$ alkyl, $C_3$-$C_6$ cycloalkyl, $C_1$-$C_3$ alkoxy, $C_1$-$C_3$ alkylthio, hydroxy or cyano, or when $R_x$ and $R_y$ are alkoxy on adjacent carbons, they combine to form a 5-membered methylene dioxy or a 6-membered ethylene dioxy ring, with the provisos that (i) when $R_4$ is hydrogen and $R_5$ is methyl, $R_x$ is hydrogen and $R_y$ is hydrogen or methyl at the 8-position, $R_2$ is not methyl or phenyl; and (ii) when $R_4$ and $R_5$ combine to form a 5-membered ring and $R_x$ and $R_y$ are hydrogen, $R_2$ is not phenyl, and the pharmaceutically-acceptable acid addition salts thereof.

The compounds of the invention may exist in different configurations and the invention is intended to embrace individual stereoisomers and mixtures thereof. However, a preferred group of compounds within the definition of Formula (I) has the β-configuration as determined by the hydrogens at positions 9b, 3a and 4 shown in Formula (II). A further preferred group has the β-configuration and also conforms to the following Formula (II):

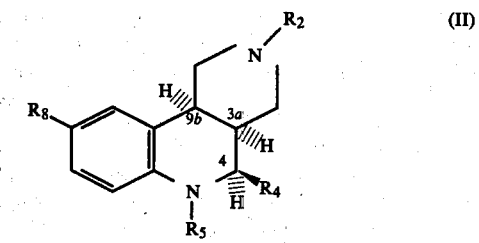

wherein $R_2$, $R_4$ and $R_5$ have the values indicated and $R_8$ is hydrogen, halogen, $C_1$-$C_6$ alkyl, $C_1$-$C_3$ alkoxy, hydroxy or cyano, and the acid addition salts thereof.

An especially preferred subgroup of compounds according to the invention comprises Formula (II) compounds or acid addition salts thereof wherein $R_2$ is hydrogen or $C_1$-$C_6$ normal alkyl, $R_4$ is hydrogen or $C_{1-C3}$ alkyl, $R_5$ is $C_1$-$C_4$ normal or branched alkyl and $R_8$ is $C_1$-$C_3$ normal or branched alkyl, $C_3$-$C_6$ branched alkyl, $C_1$-$C_3$ alkoxy, halogen (particularly fluorine, chlorine or bromine) or hydroxy.

Preferably the quinolines of the invention are prepared as salts of citric acid since these seem to be the easiest to handle and the most stable. However, other pharmaceutically acceptable acid addition salts, e.g. the hydrochlorides, hydrobromides, phosphates, sulphates, acetates and maleates, are also contemplated.

A particularly preferred compound according to the invention is one having the β-configuration represented by Formula (II), wherein $R_2$, $R_4$ and $R_8$ are each methyl, and $R_5$ is ethyl.

$R_2$ substituents in the above definition of Formula (I) may more specifically be individually chosen from the group of hydrogen; $C_1$-$C_6$ normal alkyl, preferrably $C_1$-$C_4$ normal alkyl, most preferably methyl or ethyl; $C_3$-$C_6$ cycloalkyl, preferably $C_3$-$C_4$ cycloalkyl, for example cyclopropyl and cyclopropyl methyl; $C_1$-$C_6$ hydroxyalkyl, wherein the alkyl is particularly $C_1$-$C_6$ normal alkyl or $C_3$-$C_6$ branched chain alkyl, preferrably $C_1$–$C_4$ normal- and $C_3$–$C_4$ branched chain-alkyl, for example methyl, ethyl and iso-propyl; $C_3$–$C_6$ hydroxy cycloalkyl wherein the cycloalkyl is preferably $C_3$–$C_4$ cycloalkyl, for example cyclopropyl and cyclopropyl methyl; phenyl; benzyl;

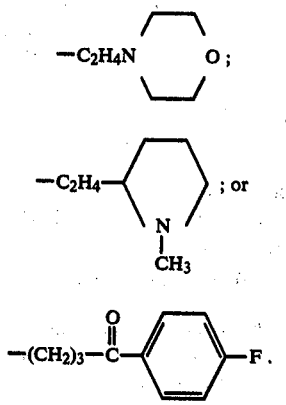

$R_4$ is chosen from the group of hydrogen; $C_1$–$C_3$ alkyl, particularly methyl and ethyl; or phenyl.

$R_5$ is chosen from the group of hydrogen; $C_1$–$C_6$ alkyl, particularly $C_1$–$C_6$ normal alkyl and $C_3$–$C_6$ branched chain alkyl, preferably $C_1$–$C_4$ normal and $C_3$–$C_4$ branched chain alkyl, for example methyl, ethyl, iso-propyl, —$CH_2CH(CH_3)_2$ and —$CH_2C(CH_3)_3$; $C_3$–$C_6$ cycloalkyl, preferably $C_3$–$C_4$ cycloalkyl, for example cyclopropyl and cyclopropyl methyl; acetyl; benzyl; and —$CH_2CF_3$.

$R_4$ and $R_5$, when alkyl, may combine to form a 5-, 6- or 7-membered ring containing the nitrogen found at Position 5 of the pyrrolo [3,4-c]quinoline.

$R_x$ and $R_y$, which may be the same or different, are chosen from hydrogen; halogen, particularly fluoro, chloro or bromo; trifluoromethyl; $C_1$–$C_6$ alkyl, particularly $C_1$–$C_6$ normal alkyl and $C_3$–$C_6$ branched chain alkyl, preferably $C_1$–$C_4$ normal and $C_3$–$C_4$ branched chain alkyl, for example methyl, ethyl, isopropyl and tert-butyl; $C_3$–$C_6$ cycloalkyl, preferably $C_3$–$C_4$ cycloalkyl, for example cyclopropyl and cyclopropyl methyl; $C_1$–$C_2$ alkoxy, particularly methoxy; $C_1$–$C_3$ alkylthio; hydroxy; and cyano.

When $R_x$ or $R_y$ is hydrogen and the other is not, the substitution other than hydrogen may be at position 6, 7, 8 or 9 of the pyrrolo [3,4-c]quinoline.

$R_x$ and $R_y$, when alkoxy, may contain to form a 5-membered methylene dioxy or 6-membered ethylene dioxy ring when situated on adjacent carbons of the aromatic ring. For example, $R_x$ and $R_y$ may represent —O—$CH_2$—O— or —O—$CH_2$—$CH_2$—O— wherein the oxygen atoms are attached to positions 6 and 7, 7 and 8 or 8 and 9 of the pyrrolo [3,4-c]quinoline. However, they may be alkoxy on adjacent carbons without combining to form a ring.

With respect to the compounds of Formulae (I) and (II) of the invention, (i) when $R_4$ is hydrogen, $R_5$ is methyl, $R_x$ or $R_y$ is hydrogen and the remainder of $R_x$ and $R_y$ is hydrogen or methyl at the 8-position, $R_2$ is not methyl or phenyl and (ii) when $R_4$ and $R_5$ combine to form a 5-membered ring and $R_x$ and $R_y$ are hydrogen, $R_2$ is not phenyl. However, the pharmaceutical compositions of the invention need not have these provisos for the active ingredient.

The compounds of the invention may be prepared in a variety of ways. References which illustrate sythetic pathways leading to useful intermediates for the compounds of the invention or the compounds themselves include W. Pftizinger, J. fur Prakt. Chemie, 56, 283 (1897); E. Campaigne and J. H. Hutchinson, J. of Heterocyclic Chem. 7, 655 (1970) and Roy et al. mentioned earlier. The following preparative methods are given for purposes of illustration:

Method I

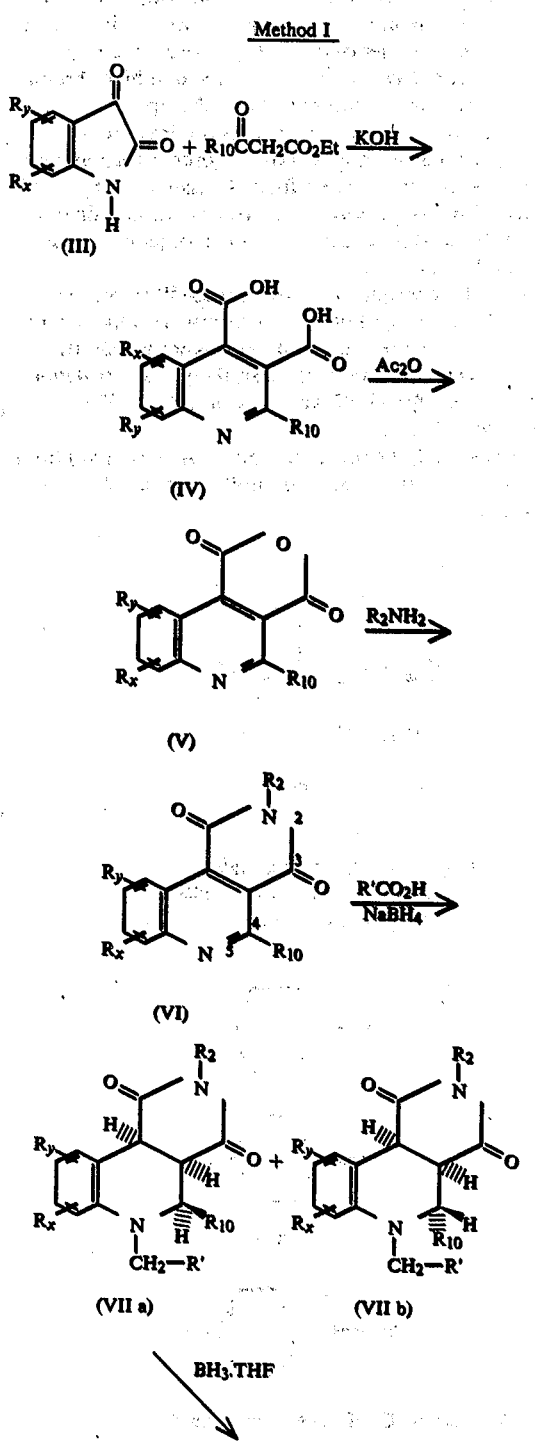

-continued
Method I

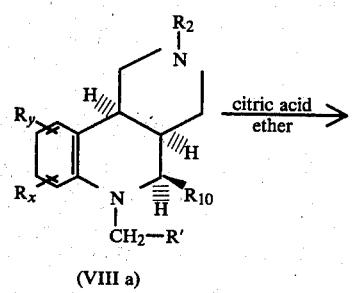

(VIII a)

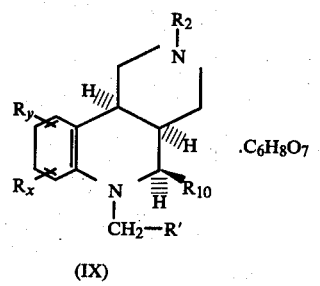

(IX)

In Method (I) above, $R_x$ and $R_y$ are as defined for Formula (I). $R_{10}$ is methyl, ethyl or phenyl $R_2$ is as defined above for Formula (I) and R' is $C_1$–$C_5$, in order to result in $C_2$–$C_6$ alkyl at position 5; hydrogen in order to produce methyl at position 5; or $CF_3$, in order to produce —$CH_2CF_3$ at position 5. Among the reagents utilized in Method I it will be appreciated by one skilled in the art that various substitutions can be made. For example, the ethyl ester $R_{10}COCH_2CO_2Et$ may be replaced by $R_{10}COCH_2CO_2CH_3$. The KOH may be replaced by NaOH, the acetic anhydride ($Ac_2O$) may be replaced by another dehydrating agent such as dicyclohexylcarbodiimide, the $NaBH_4$ may be replaced by $KBH_4$, the $BH_3$ tetrahydrofuran (THF) complex by lithium aluminum hydride and the citric acid by any of the other acids which form pharmaceutically acceptable salts.

Compounds of Formula (VI) may be additionally prepared as set forth by Ried and Weideman in Chem. Ber., 104, 3341–3349 (1971).

Method II

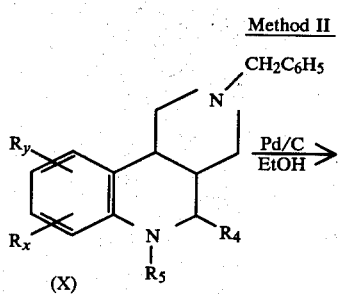

(X)

-continued
Method II

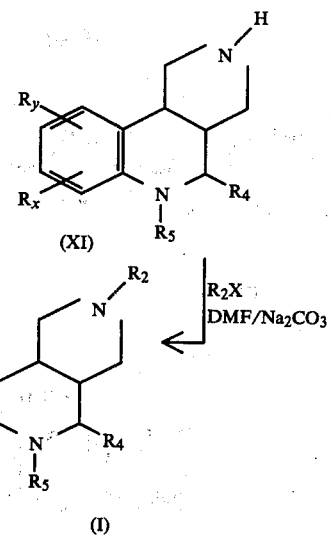

In Method II, Formula (X) compounds may be prepared by Method I leading to Formula (VIII) with the designated definitions of $R_{10}$ and R' or by combinations of Method I with Methods III, IV, V and VI. $R_2$ in Method II is as defined for Formula (I) and X is a displaceable group such as bromo or chloro. The dimethylformamide with sodium carbonate may be replaced by toluene and triethylamine.

Method III

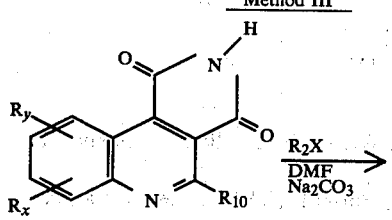

(XII)

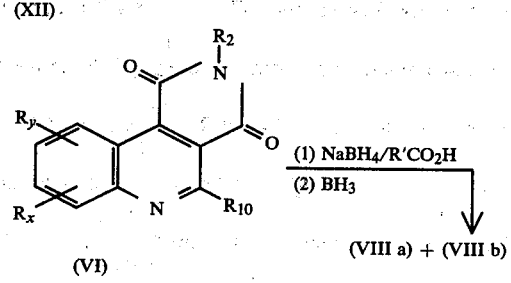

(VI)

(1) $NaBH_4/R'CO_2H$
(2) $BH_3$ (VIII a) + (VIII b)

In Method III above, Formula (VIII b) represents compounds of Formula (VIII a) with the exception that $R_{10}$ is below the molecule plane shown and is therefore of the α-configuration. As can be seen above, Method III is basically a modification of Method I wherein it is desired to change the $R_2$ substituent. Thus, compounds of Formula (XII) may be prepared by reacting those of Formula (V) with $NH_3$ in Method I.

In a modification of Method I, the intermediate formula structure (VI) can be prepared as shown in Method IV:

Method IV

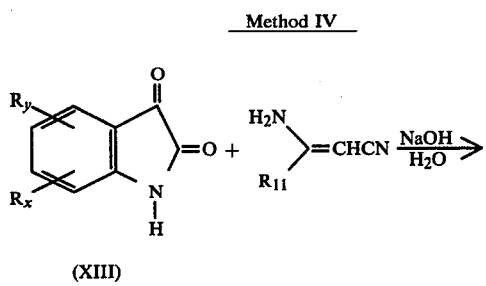

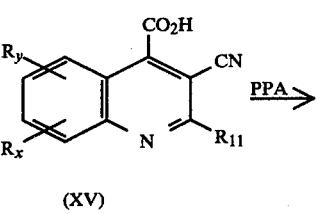

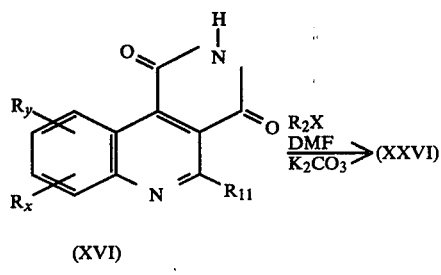

In Method IV, $R_{11}$ is $C_1$-$C_3$ alkyl or phenyl. The reaction leading to Formula (XV) is conducted at reflux for 5 hours. The reaction (XV) to (XVI) is conducted on a steambath for about 1.5 hours. $R_2X$ above is as defined in Method II. $R_x$ and $R_y$ are as defined for Formula (I). Formula (XXVI) has the same structure as Formula (VI) except that $R_{11}$ replaces $R_{10}$.

Method V

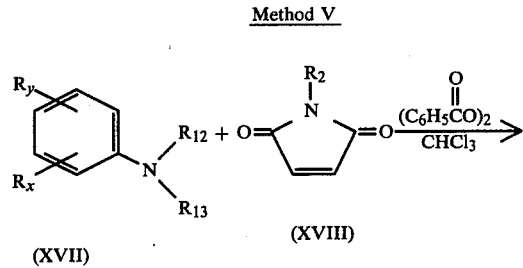

Method V

In Method V, $R_x$ and $R_y$ are as defined for Formula (I) with the exception that both cannot be ortho to the nitrogen in Formula (XVII) if both are other than hydrogen. $R_2$ in Formula (XVIII) is as defined for Formula (I). The reaction yielding Formula (XIX) may be conducted at about $-10°$ C. under nitrogen or at room temperature. $R_{12}$ and $R_{13}$ are methyl or ethyl. $R_{13}$ could be other than methyl or ethyl, e.g. H, $C_3$-$C_6$ alkyl or benzyl but a mixture might result and such would require separation of products, e.g. by chromatography. In Formulae (XIX) and (XX), $R_{14}$ is hydrogen if $R_{12}$ was methyl and is methyl if $R_{12}$ was ethyl. The reaction with $BH_3$ tetrahydrofuran complex yielding Formula (XX) may also be conducted by lithium aluminum hydride.

Method VI

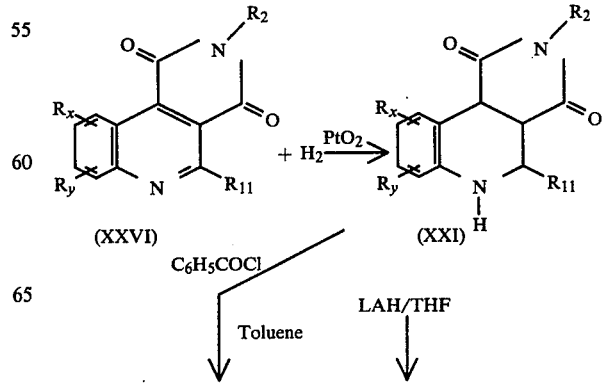

-continued
Method VI

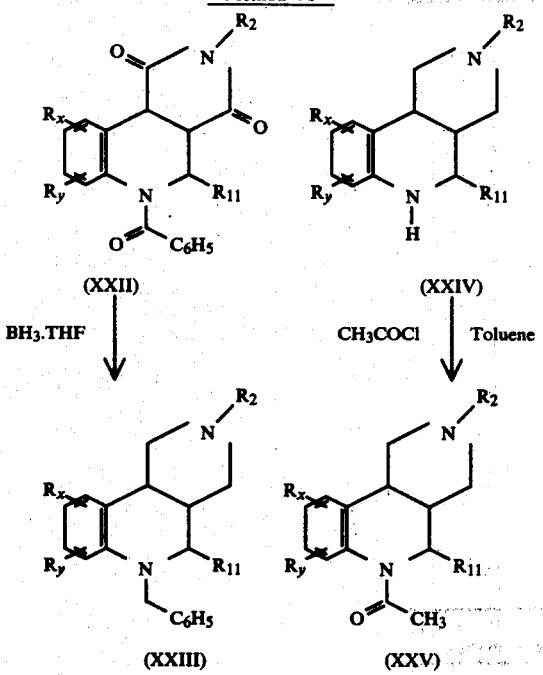

(XXII)   (XXIV)

BH₃.THF   CH₃COCl   Toluene (XXIII)   (XXV)

In Method VI, compounds within Formula (XXVI) may be prepared from Methods I, III or IV. The Formula (XXVI) compound is hydrogenated with PtO₂ in ethanol or a similar neutral solvent. The reaction of Formula (XXI) to (XXII) proceeds in toluene with triethylamine or may be conducted with toluene and 10% NaOH. The subsequent BH₃ THF reaction may be substituted by lithium aluminum hydride in order to yield Formula (XXIII). Alternatively, a Formula (XXI) compound may be reacted with an alkyl halide, such as CH₂Br, to yield alkyl at position 5. The acid chloride addition to Formula (XXIV) to yield Formula (XXV) may be conducted in toluene with 10% NaOH in water or with a toluene-triethylamine mixture.

In the above methods, modifications may be made by those skilled in the art to arrive at the compounds of the invention. For example, if the compound of Formula (I) produced has a bromine on the aromatic ring and cyano is desired, such a conversion may be carried out with a reagent such as CuCN as exemplified hereinafter.

As shown in Methods I and IV, starting materials for the present compounds are isatins of the formula

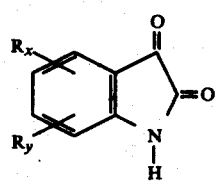

where $R_x$ is, for example, $CH_3$ and $R_y$ is H as in the case of 5-methyl isatin:

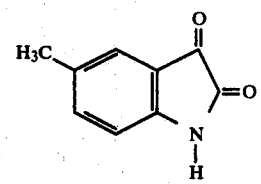

These isatins are commercially available or they may be made by the following method as given in *Org. Syn. Coll.* Vol. I, page 329:

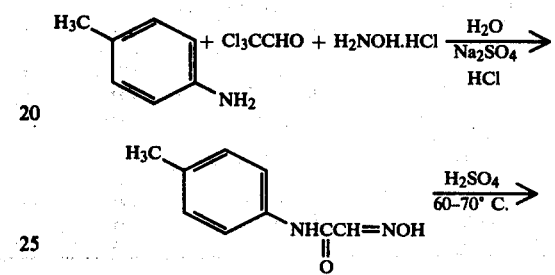

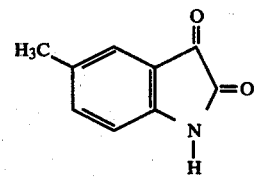

Compounds illustrative of the invention are set forth hereinafter in Table I wherein $R_2$, $R_4$, $R_5$, $R_x$ and $R_y$ have the values indicated for the structure shown, Pos represents the position of the $R_x$ and $R_y$ substituent or substituents other than hydrogen and the method of preparation is as started with reference to the methods referred to earlier herein:

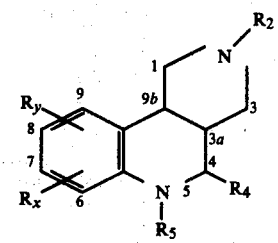

TABLE I

| Compound | $R_2$ | $R_4$ | $R_5$ | $R_x$ | Pos | Preparation Method |
|---|---|---|---|---|---|---|
| 1 | CH₃ | CH₃ | C₂H₅ | Cl | 8 | I |
| 2 | CH₃ | CH₃ | C₂H₅ | H | — | I |
| 3 | CH₃ | CH₃ | C₂H₅ | CH₃ | 8 | I |
| 4 | CH₃ | CH₃ | C₂H₅ | OCH₃ | 8 | I |
| 5 | CH₃ | CH₃ | C₂H₅ | F | 8 | I |

TABLE I-continued

| Compound | R₂ | R₄ | R₅ | Rₓ(Rᵧ) | Pos Rₓ(Rᵧ) | Preparation Method |
|---|---|---|---|---|---|---|
| 6 | $CH_3$ | $CH_3$ | $C_2H_5$ | Cl | 7 | I |
| 7 | $CH_3$ | $CH_3$ | $C_2H_5$ | OH | 8 | I |
| 8 | $CH_3$ | $CH_3$ | $C_2H_5$ | Br | 8 | I |
| 9 | $CH_3$ | $CH_3$ | $C_2H_5$ | iso-$C_3H_7$ | 8 | I |
| 10 | $CH_3$ | $CH_3$ | $C_2H_5$ | $C_2H_5$ | 8 | I |
| 11 | $CH_3$ | $CH_3$ | $C_2H_5$ | CN | 8 | I |
| 12 | $CH_3$ | $CH_3$ | $C_2H_5$ | n-$C_4H_9$ | 8 | I |
| 13 | $CH_3$ | $CH_3$ | $C_6H_5$ | $CH_3$ | 8 | I |
| 14 | $CH_3$ | $C_6H_5$ | $C_2H_5$ | H | — | I |
| 15 | $CH_3$ | $C_2H_5$ | $C_2H_5$ | $CH_3$ | 8 | I |
| 16 | $CH_3$ | $CH_3$ | n-$C_3H_7$ | Cl | 8 | I |
| 17 | $CH_3$ | $CH_3$ | n-$C_3H_7$ | $CH_3$ | 8 | I |
| 18 | $CH_3$ | $CH_3$ | $CH_3$ | $CH_3$ | 8 | I |
| 19 | H | $CH_3$ | $CH_3$ | $CH_3$ | 8 | I |
| 20 | H | $CH_3$ | $C_2H_5$ | $CH_3$ | 8 | I |
| 21 | $CH_2$-$C_6H_5$ | $CH_3$ | $C_2H_5$ | $CH_3$ | 8 | I |
| 22 | iso-$C_3H_7$ | $CH_3$ | $C_2H_5$ | $CH_3$ | 8 | I |
| 23 | $C_2H_4CH$ | $CH_3$ | $C_2H_5$ | $CH_3$ | 8 | I |
| 24 | cyclo-$C_4H_7$ | $CH_3$ | $C_2H_5$ | $CH_3$ | 8 | I |
| 25 | $C_2H_5$ | $CH_3$ | $C_2H_5$ | $CH_3$ | 8 | I |
| 26 | $C_2H_4N$(morpholino) | $CH_3$ | $C_2H_5$ | $CH_3$ | 8 | I |
| 27 | $C_2H_5$ | $CH_3$ | $C_2H_5$ | $C_2H_5$ | 8 | I |
| 28 | $(CH_2)_2$-(N-methylpyrrolidinyl) | $CH_3$ | $C_2H_5$ | $CH_3$ | 8 | III |
| 29 | $(CH_2)_3C(O)$-$C_6H_4$-F | $CH_3$ | $C_2H_5$ | $CH_3$ | 8 | II |
| 30 | $CH_3$ | $CH_3$ | $CH_2CH_3$ | $CH_3(CH_3)$ | 7(8) | I |
| 31 | $CH_3$ | $CH_3$ | $CH_2CF_3$ | $CH_3$ | 8 | I |
| 32 | $CH_3$ | $CH_3$ | H | Cl(OCH₃) | 9(6) | IV |
| 33 | $CH_3$ | $CH_3$ | $C_2H_5$ | Cl(OCH₃) | 9(6) | IV |
| 34 | $CH_3$ | H | $C_2H_5$ | $CH_3$ | 8 | V |
| 35 | $CH_3$ | $CH_3$ | H | Cl(Cl) | 6(8) | I |
| 36 | $CH_3$ | H | $CH_3$ | $CH_3$ | 8 | V |
| 37 | $CH_3$ | $CH_3$ | $CH_2CH(CH_3)_2$ | $CH_3$ | 8 | I |
| 38 | $CH_3$ | $CH_3$ | $CH_2CH(CH_3)_2$ | $CH_3(CH_3)$ | 7(8) | I |
| 39 | $CH_3$ | $CH_3$ | $CH_2C_6H_5$ | $CH_3$ | 8 | VI |
| 40 | $CH_3$ | $CH_3$ | H | $CH_3$ | 8 | VI |
| 41 | $CH_3$ | $CH_3$ | $CH_2C(CH_3)_3$ | $CH_3$ | 8 | VI |
| 42 | $CH_3$ | H | $CH_3$ | $C(CH_3)_3$ | 8 | V |
| 43 | $CH_3$ | $CH_3$ | $OC(O)CH_3$ | $CH_3$ | 8 | VI |
| 44 | $CH_3$ | $CH_3$ | $C_2H_5$ | $OCH_3$ | 6 | V |
| 45 | $CH_3$ | —$(CH_2)_3$— | | $CH_3$ | 8 | V |
| 46 | $CH_3$ | —$(CH_2)_4$— | | $CH_3$ | 8 | V |
| 47 | $CH_3$ | $CH_3$ | $C_2H_5$ | $OC_2H_5$ | 8 | V |
| 48 | $CH_3$ | H | $CH_3$ | Cl | 9 | V |

The following specific examples serve to further illustrate the invention. Unless otherwise given, all temperatures are in degrees Centigrade and NMR data is in parts per million relative to tetramethylsilane as an internal standard:

EXAMPLE 1

(Method I)

2,6-dimethylquinoline-3,4-dicarboxylic acid (i)

To a 2 liter 3-neck flask fitted with a magnetic stirring bar, thermometer, reflux condenser, N₂ inlet tube, and dropping funnel was charged 73 g (0.45 mole) of 5-methylisatin, 300 g KOH and 1100 ml H₂O while maintaining a N₂ atmosphere. The dark solution was maintained at 55° while 164 g (1.26 moles) of ethyl acetoacetate were added dropwise over a period of 3 hours. When addition was complete the internal temperature was raised to 85° and held for 45 minutes. The reaction was then stirred at ambient temperature for 2 days.

Acidification of the reaction mixture by dropwise addition of 400 ml of concentrated HCl over a period of 2.25 hours while maintaining the internal temperature at approximately 20°, gives a tan solid that was collected by filtration, washed with H₂O and dried in vacuum; yield, 99.8 g (90% of theoretrical).

2,6-dimethylquinoline-3,4-dicarboxylic acid anhydride (ii)

A 2 L round bottom flask fitted with a magnetic stirring bar, reflux condenser, and drying tube was charged with 70 g (0.285 mole) of (i) and 1 L of reagent grade acetic anhydride. The tan suspension was stirred at reflux for 23 hours.

The Ac₂O was removed in vacuo using a rotary evaporator and the resulting dark solid was triturated with 500 ml of ether. The solid was collected on a filter and dried; yield 58 g (89.4%).

The ether filtrate was concentrated on a rotary evaporator, affording an additional 5.4 g (8.3%) of product; total yield, 63.4 g (97.7%).

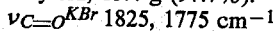
$v_{C=O}^{KBr}$ 1825, 1775 cm⁻¹

1,3-dioxo-2,4,8-trimethyl-2H-pyrrolo [3,4-c]quinoline (iii)

A 2 L round bottom flask fitted with a magnetic stirring bar, reflux condenser, and drying tube was charged with 59 g (0.26 mole) of (ii), 1 L of dry pyridine and cooled with an ice bath. To the cool mixture was added a slight excess of dry reagent grade methyl amine (9.3 g required). The dark mixture was warmed to room temperature and then refluxed for 20 hours with efficient stirring.

The reaction mixture was allowed to cool and the pyridine removed in vacuo on a rotary evaporator. The dark solid so obtained was triturated with toluene and evaporated in vacuo to remove the last traces of pyridine. The toluene treatment was followed by trituration with ether and the solid filtered; yield, 56 g. Concentration of the ether filtrate afforded an additional 4 g; total yield, 60 g (96%).

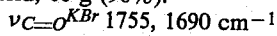
$v_{C=O}^{KBr}$ 1755, 1690 cm⁻¹

1,3-dioxo-5-ethyl-3aα,4α,5,9bα-tetrahydro-2,4,8-trimethyl-2-H-pyrrolo [3,4-c]quinoline (iva) and 1,3-dioxo-5-ethyl-3aα, 4β, 5,9bα-tetrahydro-2,4,8-trimethyl-2-H-pyrrolo [3,4-c]quinoline (ivb)

A 1 L 3-neck flask fitted with a thermometer reflux condenser, magnetic stirring bar and flushed with N₂ was charged with 15 g (0.0624 mole) of (iii) and 550 ml of glacial acetic acid (glac. HOAc). The brown solution was cooled to 15° and 23.7 g (0.624 mole) of reagent grade NaBH₄ added portionwise over a period of 1.5 hours holding the internal temperature between 15°-20°. The reaction mixture was stirred overnight at room temperature then refluxed for 1 hour.

The reaction mixture was cooled, transferred to a 2 L beaker, diluted with 1 L cold H₂O and adjusted to pH 10-12 with approximately 500 ml of 50% NaOH. The suspension was extracted with 3×250 ml portions of ether and 3×250 ml portions of ethyl acetate (EtOAc). The organic extracts were combined, dried (Na₂SO₄) and evaporated to dryness in vacuo to give 14.8 g of a red-brown oil that partially solidified on standing at room temperature.

The crude material was purified by column chromatography on 300 g of silica gel using ether/hexane and gradient elution. The epimer (iva) eluted first (10% ether) and was isolated as buff-colored needles; yield, 7.1 g (42%) NMR (CDCl₃) 0.81 [d, J=6.5 Hz, 4-CH₃]; KBr C=O 1760, 1675 cm⁻¹.

A mixture of (iva) and (ivb) was next eluted; yield, 1.25 g (7.35%).

Epimer (ivb), 1 g (5.8%), eluted with 20% ether and was isolated as a light red solid; NMR(CDCl₃) 0.96-1.24 [m,4-CH₃, 5-ethyl-CH₃]; KBr C=O 1775, 1690 cm⁻¹.

5-ethyl-1,3,3aα,4α5,9bα-hexahydro-2,4,8-trimethyl-2H-pyrrolo [3,4-c]quinoline (va) (Compound 3 on Table I)

To a 500 ml 3-neck flask fitted with a thermometer, reflux condenser, N₂ inlet tube, and magnetic stirring bar was added a solution of 7 g (0.0257 mole) of (iva) in 50 ml of anhydrous reagent grade THF. The apparatus was purged with N₂ and cooled to 0° by means of an ice bath while 270 ml of a 0.94 M solution of BH₃ THF in THF was added dropwise over a 20 minute period. The ice bath was removed and the reaction was refluxed for 18 hours under N₂.

Approximately 100 ml of the THF was distilled at atmospheric pressure and the reaction cooled by means of an ice bath. The reaction was quenched by adding 100 ml of cold H₂O followed by 120 ml of 6 M HCl over a 10 minute period. The remaining THF was distilled at atmospheric pressure. The aqueous phase was made alkaline (pH 10-12) with 20% NaOH and the white mixture extracted with 5×150 ml portions of ether. The extracts were combined, dried (Na₂SO₄), and evaporated in vacuo to give 6.3 g of crude yellow oil. Bulb to bulb distillation of the crude oil gave 5.8 g (93%) of a colorless oil; boiling point (bp) 110°-115°/0.1 mm Hg.

NMR(CDCl₃) 0.99-1.19 [m,4-CH₃, 5-CH₂CH₃], 2.20 [s, 8-CH₃], 2.29 [s, 2-CH₃]; M/e⊕, 244.

citrate of (va)

A solution of 5.7 g (0.0209 mole) of (va) in 100 ml of anhydrous reagent grade ether was treated portionwise with 4.03 g (0.021 mole) of citric acid in 800 ml of ether with vigorous stirring. The precipitated citrate salt was filtered, washed with ether and dried in vacuo at 50° C., yield, 9.2 g (95%), melting point (mp) 129°-131° (dec.).

Anal for C₁₆H₂₄N₂·C₆H₈O₇: Calculated: C, 60.53; H, 7.39; N, 6.42: Found: C, 60.67; H, 7.33; N, 6.19.

5-ethyl-1,3,3aα,4α,5,9bα-hexahydro-2,4,8-trimethyl-2H-pyrrolo[3,4-c]quinoline (vb)

(ivb) was converted to (vb) in 84% yield by the procedure described above for (va).

citrate of (vb)

The citrate salt of (vb) was prepared by the procedure described above for preparing the citrate salt of (va) mp 152°-153°.

Anal for C₁₆H₂₄N₂·C₆H₈O₇: Calculated: C, 60.53; H, 7.59; N, 6.42: Found: C, 60.75; H, 7.33; N, 6.16.

EXAMPLE 2
(Method IV)

3-cyano-2,6-dimethyl quinoline-4-carboxylic acid (vi)

A warm solution of 5-methylisatin (25 g, 0.155 mole) in 400 ml H$_2$O containing 6.2 g (0.155 mole) of NaOH was treated with 12.7 g (0.155 mole) of 3-aminocrotononitrile in 3 approximately equal portions. The reaction mixture was refluxed for 5 hours and then stirred at ambient temperature overnight.

The reaction mixture was cooled and acidified to pH 3 with 25 ml of 12% HCl. The precipitate was filtered, washed, with H$_2$O and dried in vacuum; yield, 16.4 g (47%).

$\nu_{CN}^{KBr}$ 2200 cm$^{-1}$, $\nu_{COOH}^{KBr}$ 1690 cm$^{-1}$

1,3-dioxo-4,8-dimethyl-2H pyrrolo[3,4-c]quinoline (vii)

A mixture of 16.4 g (0.07 mole) of (vi) and 175 g of polyphosphoric acid was heated on a steam bath with intermittent mechanical stirring for 1.5 hours. The warm reaction mixture was poured onto 1 L of ice/water with stirring. After standing overnight, the mixture was clarified by filtration through Celite and the filtrate adjusted to pH 4 with NaOH pellets. The resulting solid was filtered, washed with H$_2$O and dried in a vacuum oven at 50° C.

$\nu_{NH}^{KBr}$ 300 cm$^{-1}$, $\nu_{C=O}^{KBr}$ 1760, 1720 cm$^{-1}$

Preparation of Compound (iii) from Compound (vii)

To a stirred suspension of 6.6 g (0.029 mole) of (vii), and 4.0 g (0.029 mole) of potassium carbonate in 75 ml anhyd. dimethyl formamide (DMF) was added in one portion 20.6 g (0.145 mole) of CH$_3$I. The reaction mixture was protected from atmospheric moisture and stirred 24–28 hours.

The solid was filtered, washed with H$_2$O and dried in a vacuum oven at 50° C. Yield, 5.1 g; mp 159°–162° C.

$\nu_{C=O}^{KBr}$ 1775, 1690 cm$^{-1}$.

This spectrum was identical to that of (iii) prepared by Method I in Example 1.

EXAMPLE 3

6-bromo-2-methylquinoline-3,4-dicarboxylic acid (viii)

A 1 L 3-neck flask fitted with a magnetic stirrer, reflux condenser, thermometer, and dropping funnel was charged with 50 g (0.221 mole) of 5-bromoisatin, 150 g of KOH and 540 ml of H$_2$O. The dark solution was maintained at 60° while 80.8 g (0.621 mole) of ethyl acetoacetate was added dropwise over a period of 2 hours. When addition was complete the internal temperature was raised to 90° and refluxed for 1 hour. The solution was cooled and stirred at room temperature for 2 days.

The reaction mixture was poured onto 1 liter of cracked ice and acidified over a period of 1 hour with 200 ml of concd. HCl. The resulting suspension was diluted with 1 liter of H$_2$O, and the solid was filtered, washed with H$_2$O and dried; yield, 66.04 g (96.0%).

6-bromo-2-methylquinoline-3,4-dicarboxylic acid anhydride (ix)

A 1 liter round-bottom flask with a magnetic stirring bar, reflux condenser and drying tube was charged with 16 g (0.0516 mole) of (viii) and 250 ml of reagent grade Ac$_2$O. The mixture was stirred and refluxed for 18 hours.

The excess Ac$_2$O was evaporated in vacuo on a rotary evaporator and the residual material was triturated with ether, filtered and dried in vacuo giving 14.7 g of crude product.

1,3-dioxo-2,4-dimethyl-8-bromo-2H-pyrrolo [3,4-c]quinoline (x)

To 350 ml of dry pyridine was added 14.7 g of the anhydride (ix) in a 3-neck flask with reflux condenser, drying tube, magnetic stirrer and a thermometer. The flask was cooled with an ice/H$_2$O bath and dry reagent grade CH$_3$NH$_2$ was passed into the mixture. The flask was then allowed to warm up to room temperature and refluxed for 20 hours.

The pyridine was evaporated in vacuo. The recovered dark syrup was triturated with ether and the solids filtered to give 15.2 g of product.

8-bromo-2,4-dimethyl-1,3-dioxo-5-ethyl-3aα,4α,5,9bα-tetrahydro-2-H-pyrrolo[3,4-c]quinoline (xi)

A 1 liter 3-neck flask fitted with a magnetic stirrer reflux condenser and N$_2$ T-tube, and thermometer was charged with 22.1 g (0.0724 mole) of (x) in 750 ml of glac. HOAc. The flask was cooled by an ice/water bath and flushed with N$_2$ gas. NaBH$_4$ (28 g; 0.724 mole) was added portionwise over 1 hour while maintaining efficient stirring, an internal temperature of 15°–20° and a constant N$_2$ gas purge. The thick red-brown mass was stirred at room temperature for 20 hours and refluxed for 2 hours under N$_2$. NOAc, 250 ml, was distilled, the flask cooled in an ice/water bath, and the mixture was neutralized with 200 ml of 50% NaOH. The thick mixture was extracted with EtOAc. The EtOAc extract was washed with H$_2$O, dried (Na$_2$SO$_4$) and evaporated to dryness to give (xia) and (xib).

Twenty grams of red-brown syrup was recovered that was purified on 300 g of silica gel by gradient elution with ether/hexane (7 to 30%) to give 11 g of (xia) as a beige solid.

8-bromo-2,4-dimethyl-5-ethyl-1,3,3aα,4α,5,9bα-hexahydro-2H-pyrrolo[3,4-c]quinoline (xiia) (Compound 8 on Table I)

A 1 liter 3-neck flask fitted as above and purged with N$_2$ was charged with 11 g (0.0305 mole) of (xia) and 240 ml of dry THF. A 360 ml solution of 0.9 M BH$_3$.THF (0.325 mole) was added dropwise over a 15 minute period with efficient stirring. The mixture was refluxed for 60 hours under N$_2$, cooled in an ice/water bath, and quenched with 125 ml H$_2$O and 75 ml of 6 M HCl. The THF was distilled at atmospheric pressure. The remaining aqueous phase was made alkaline with 50% NaOH (ice cooling) and extracted with ether. The combined ether extracts were washed with H$_2$O, dried (Na$_2$SO$_4$) and evaporated in vacuo giving 12.4 g of crude oil. Bulb to bulb distillation of the oil gave 8.51 g (85%) of yellow oil.

8-cyano-2,4,-dimethyl-5-ethyl-1,3,3aα,4α,5,9bα-hexahydro-2H-pyrrolo[3,4-c]quinoline (xiiia) (Compound 11 on Table I)

A mixture of 3.09 g of (xiia) (0.01 mole) 1.95 g (0.021 mole) CuCN and 50 ml of dry reagent grade N-methyl-2-pyrrolidone was refluxed with stirring under N$_2$ for 8 hours. The flask was cooled, the mixture filtered, and filtrate poured into 400 ml of 5 M NaCN/H$_2$O. The aqueous phase was extracted repeatedly with EtOAc, the extracts combined, and dried (MgSO$_4$). Evaporation and bulb to bulb distillation gave 1.53 g (60%) of oil (b.p. 160°–165° 0.1 torr). Conversion of the oil to its citrate salt in ether gave a light yellow powder, mp 93°–96° (dec).

Anal. for $C_{16}H_{21}N_3 \cdot C_6H_8O_7$: Calcd: C, 59.05; H, 6.53; N, 9.39: Found: C, 59.38; H, 6.43; N, 9.42.

EXAMPLE 4

6-methoxy-2-methylquinoline-3,4-dicarboxylic acid (xiv)

A solution of 59.4 g (0.335 mole) of 5-methoxyisatin, 225 g KOH in 800 ml $H_2O$ was treated dropwise with 121.4 g (0.932 mole) of ethylacetoacetate at 55° over a 2 hour period. The solution was refluxed 45 minutes and stirred 2 days at room temperature. Acidification with 300 ml concd. HCl while maintaining the temperature at ambient conditions gave a tan solid that was filtered, washed with $H_2O$ and dried; yield 60.8 g (69.4%).

2,4-dimethyl-1,3-dioxo-8-methoxy-2H-pyrrolo[3,4-c]quinoline (xv)

A solution of 60.8 g (0.233 mole) of (xiv) in 1 liter of reagent grade $Ac_2O$ was refluxed for 6 hours. Distillation of excess $Ac_2O$, trituration of the residue with ether, and filtration gave 59.2 g of the anhydride.

A mixture of 40 g (0.164 mole) of the anhydride and 750 ml of dry xylene was cooled and $CH_3NH_2$ bubbled into the stirred suspension for 20 minutes. The reaction was then slowly heated to reflux (1 hour) and refluxing continued for 24 hours. The reaction was filtered while hot and the filtrate evaporated to dryness giving 21 g of product (xv).

2,4-dimethyl-1,3-dioxo-5-ethyl-8-methoxy-3a$\alpha$,4$\alpha$,5,-9b$\alpha$tetrahydro-2H-pyrrolo[3,4-c]quinoline (xvia)

To 9 g (0.035 mole) of the pyrrolo [3,4c]quinoline (xv) in 250 ml glac. HOAc and 24 ml dry THF under $N_2$, ice cooling and efficient stirring, was added, portionwise, 13.25 g (0.35 mole) of $NaBH_4$ at such a rate that an internal temperature of 10°–15° was maintained. The mixture was stirred at ambient temperature for 72 hours, refluxed 1 hour and finally made alkaline with 50% NaOH keeping the temperature at 20°. The resulting mixture was extracted with several portions of ether, which were combined, dried ($Na_2SO_4$) and evaporated in vacuo to give 8.3 g of product after triturating with hexane.

2,4-dimethyl-5-ethyl-8-methoxy-1,3,3a$\alpha$,4$\alpha$,5,9b$\alpha$-hexahydro-2H-pyrrolo[3,4-c]quinoline (xviia) (Compound 4 on Table I)

To a solution of 8.3 g (0.0288 mole) of the dioxo intermediate (xvia) in 200 ml of dry THF under $N_2$ was added 305 ml (0.29 mole) of a 0.94 M solution of $BH_3 \cdot THF$ in THF with efficient stirring and external ice cooling. The solution was refluxed under $N_2$ for 20 hours, cooled and quenched by dropwise addition of 175 ml $H_2O$ and 125 ml of 6 M HCl. Excess THF was distilled at atmospheric pressure, the aqueous residue was adjusted to pH 9 with 15% NaOH and the suspension extracted with ether. The ether was dried ($Na_2SO_4$) evaporated in vacuo and the crude oil purified by bulb to bulb distillation at 125°–130° and 0.1 torr.

2,4-dimethyl-5-ethyl-1,3,3a$\alpha$,4$\alpha$,5,9b$\alpha$-hexahydro-8-hydroxy-2H-pyrrolo[3,4-c]quinoline (xviiia) (Compound 7 on Table I)

A solution of 2.14 g (0.0082 mole) of the 8-methoxy (xviia) in 40 ml of 48% HBr was refluxed under $N_2$ for 24 hours. The cooled solution was basified to pH 9 with concd. $NH_4OH$ and the cloudy mixture extracted repeatedly with EtOAc (9×100 ml). The combined extracts were dried ($Na_2SO_4$) and reduced to dryness giving 1.57 g of a yellow-brown syrup. Conversion to the citrate salt with 1.2 g of citric acid in THF/ether/methanol (MeOH) (1:4:0.05) gives 1.75 g of product, mp 65°–70° (dec).

Anal. for $C_{15}H_{22}N_2O \cdot C_6H_8O_7 \cdot \frac{1}{2} H_2O$: Calculated: C, 56.36; H, 6.98; N, 6.26: Found: C, 56.65; H, 7.20; N, 6.10.

EXAMPLE 5

Method II 4,8-dimethyl-5-ethyl-1,3,3a$\alpha$,4$\alpha$,5,9b$\alpha$-hexahydro-2H-pyrrolo[3,4-c]quinoline (xix) (Compound 20 on Table I)

A mixture of 6 g (0.0187 mole) of (xx) of the Formula (VIIIa) with $R_2$=benzyl, $R_{10}$=methyl, R'=methyl, $R_x$=H and $R_y$=methyl at position 8 prepared by Method (I), 1.5 g of 10% Pd/C, and 180 ml of absolute ethanol was shaken in an atmosphere of $H_2$ at an initial pressure of 50 psig at 40° for 17 hrs. The catalyst was removed by filtration and the filtrate concentrated to dryness in vacuo on a rotary evaporator. The residual yellow oil was Kugelrohr distilled at 105°–115° and 0.2 torr; yield, 3.85 g.

γ-(4,8-dimethyl-5-ethyl-1,3,3a$\alpha$,4$\alpha$,5,9b$\alpha$-hexahydro-2H-pyrrolo[3,4-c]quinoline-2-yl)-p-fluorobutyrophenone (xxi) (Compound 29 on Table I)

A mixture of 1.5 g (6.5 mmoles) of (xix), 1.34 g (6.7 mmoles) of γ-chloro-p-fluorobutyrophenone, 0.66 g (6.5 mmoles) of triethylamine, and 75 ml of dry toluene was refluxed for 47 hours under $N_2$.

The toluene was clarified by filtration and removed in vacuo on a rotary evaporator. The residual brown oil was dissolved in ether and extracted with 10% HCl. The aqueous extract was made alkaline with aqueous NaOH and extracted with ether. The ether phase was dried ($Na_2SO_4$) and reduced to dryness on a rotary evaporator in vacuo; yield 2.1 g of brown oil.

The brown oil was filtered through a column of neutral alumina in 1:1 ether/hexane giving 1.05 g of pure material. Conversion to a citrate salt as described above gave 1.3 g of product, mp 65°–70°.

EXAMPLE 6

Method III 4,8-dimethyl-1,3-dioxo-2-(2-morpholinoethyl)-2H-pyrrolo[3,4-c]quinoline (xxii)

A mixture of 5 g (0.022 mole) of 1,3-dioxo-4,8-dimethyl-2H-pyrrolo [3,4-c]quinoline (vii) (also known as 2,6-dimethyl quinoline 3,4-dicarboximide), 4.65 g (0.025 mole) of N-(2-chloroethyl) morpholine, 6.9 g (0.05 mole) $K_2CO_3$, and 50 ml of dry DMF was stirred and heated at 50° for 18 hours. The dark mixture was poured into $H_2O$ with stirring and the solids filtered; yield, 6 g after drying in vacuo.

4,8-dimethyl-1,3-dioxo-5-ethyl-2(2-morpholinoethyl)-3a$\alpha$,4$\alpha$,5,9b$\alpha$-tetrahydro-2H-pyrrolo[3,4-c]quinoline (xxiii)

To a cool solution of 6 g (0.0177 mole) of the pyrrolo [3,4-c]quinoline (xxii) in 140 ml of glac. HOAc under $N_2$ was added 6.7 g (0.177 mole) of $NaBH_4$ at such a rate that the internal temperature did not rise above 20°. The reaction mixture was stirred for 18 hours at ambient temperature then refluxed for 1.5 hours under $N_2$. Excess HOAc was removed in vacuo on a rotary evaporator and the residual syrup was treated with ice water and 30% NaOH solution until strongly basic.

The aqueous mixture was extracted with $CH_2Cl_2$. The $CH_2Cl_2$ extracts were washed with $H_2O$, dried ($Na_2SO_4$) and evaporated in vacuo leaving 4.3 g of a dark gum.

The dark gum was chromatographed on silica gel (Woelm, act. grade III) eluting with 30% ether/hexanes and ethyl acetate; yield, 2.6 g of red-brown syrup.

4,8-dimethyl-5-ethyl-1,3,3aα,4α,5,9bα-hexahydro 2-(2-morpholinoethyl)-2H-pyrrolo [3,4-c]quinoline (xxiv) (Compound 26 on Table I)

A cold solution of 40 ml of 0.94 M $BH_3$.THF under $N_2$ was added dropwise to a cold, stirred solution of 2.6 g of the above pyrrolo [3,4-c]quinoline (xxiii) in 40 ml of dry THF. The solution was refluxed under $N_2$ for 4 hours. Excess $BH_3$ was destroyed by adding 20 ml of cold $H_2O$ and 50 ml of 6 M HCl to the cooled solution under $N_2$. Excess THF was distilled at atmospheric pressure. The aqueous mother liquor was rendered strongly akaline with 50% NaOH solution and extracted with ether. The ether extracts were washed with $H_2O$, dried ($Na_2SO_4$) and reduced to dryness in vacuo on a rotary evaporator leaving 1.85 g of syrup.

The crude syrup was converted to a citrate salt (1.03 g citric acid) in ether as described above.

The crude citrate salt was crystallized from absolute ethanol/ether; yield, 2.2 g, mp 65° (decomp).

EXAMPLE 7

Method V 2,9-dimethyl-1,3-dioxo-3aα,3bα,6a,10bα-tetrahydro pyrrolo[1,2-a]-2H-pyrrolo[3,4-c]quinoline (xxv)

A solution of 7.65 g (0.0316 mole) of benzoyl peroxide in 150 ml of dry $CHCl_3$ was added dropwise (3 hrs) to a stirred solution of 11.35 g (0.0704 mole) of N-(p-tolyl) pyrrolidine and 3.17 g (0.0285 mole) of N-methyl maleimide under $N_2$ and cooled to $-10°$.

After storing at $-10°$ for 15 hrs., 125 ml of 25% NaOH solution was added over 20 min. and the mixture was stirred ½ hrs. at 0°. An additional 100 ml of $H_2O$ was added and the $CHCl_3$ phase separated. The aqueous mother liquor was extracted with $CHCl_3$ and the combined $CHCl_3$ extracts were backwashed with $H_2O$ and dried ($Na_2SO_4$). Removal of the $CHCl_3$ in vacuo on a rotary evaporator left 14 g of crude oil.

The crude oil was chromatographed on silica gel (Woelm, act. grade III distributed by ICN Pharmaceuticals, Cleveland, Ohio) eluting with 25% ether/hexanes. The desired material (1.5 g) was obtained contaminated with a small amount of 2-benzoyloxy-N-(p-tolyl)pyrrolidine.

EXAMPLE 8

2,9-dimethyl-1,3,3aα,3bα,6a,10bα-hexahydro-pyrrolo[1,2-a]-2H-pyrrolo[3,4-c]quinoline (xxvi)

A cold solution of 57 ml of 0.94 M $BH_3$.THF in THF was added over 10 min. under $N_2$ to a cold solution of 1.46 g (0.0054 mole) of the imide (xxv) produced in Example 7 in 75 ml of dry THF. The solution was stirred and refluxed for 24 hours under $N_2$. Excess $BH_3$ was destroyed by dropwise addition of 25 ml of $H_2O$ and 50 ml 6 M HCl. THF was distilled at atmospheric pressure and the remaining aqueous phase was made strongly alkaline with 15 ml of 50% NaOH solution. The aqueous layer was extracted with ether. The ether extracts were dried ($Na_2SO_4$) and reduced to dryness in vacuo on a rotary evaporator leaving 1.5 g of brown oil. Bulb-to-bulb distillation of the oil (bp 107°–111° at 0.3 mm) gave 0.86 g of a rose-colored oil. Conversion to the citrate salt gave 1.48 g of solid, mp 104°–108°.

EXAMPLE 9

4,8,dimethyl-1,3-dioxo-5-ethyl-3aα,4α,5,9bα-tetrahydro-2H-pyrrolo[3,4-c]quinoline (xxvii)

Sodium borohydride (19.6 g) was added portionwise under $N_2$ to a stirred solution of 11.75 g of 2,6-dimethyl quinoline-3,4-dicarboximide in 400 ml of glac. HOAc. The internal temp. was maintained at or below 20°. The dark mixture ws refluxed for 4 hours then excess HOAc was distilled in vacuo. The residual syrup was treated with 80 ml of cold $H_2O$ and rendered alkaline with 30% NaOH soln. A thick sludge formed that was extracted into 175 ml of $CH_2Cl_2$. The $CH_2Cl_2$ was separated, washed with $H_2O$ and dried ($Na_2SO_4$). Removal of the $CH_2Cl_2$ in vacuo on a rotary evaporator left a dark gum that was chromotographed on silica gel (Woelm, act. grade III) by gradient elution with 1–25% EtOAc/hexane; yield, 5 g.

4,8-dimethyl-1,3-dioxo-5-ethyl-3aα,5,9bα-tetrahydro-2-(N-methylpyrrolidin-2-ylethyl)-2H-pyrrolo[3,4-c]quinoline (xxviii)

A solution of 3.64 g (19.8 mmoles) of 2-(2-chloroethyl)-1-methylpyrrolidine hydrochloride in 10 ml DMF was added to a stirred mixture of 5 g (19.8 mmoles) of the compound of Formula (VIIa) with $R_2$=H, $R_4$=-$CH_3$, R'=-$CH_3$, $R_x$=-$CH_3$ at C-8 and $R_y$=H, 4.24 g (40 mmoles) $Na_2CO_3$, and 50 ml of dry DMF. The reaction mixture was stirred at ambient temp for 20 hours then at 90° for 2 hours.

Inorganic salts were filtered and the filtrate was reduced to dryness in vacuo on a rotary evaporator to give 8 g of red gum. The gum was chromatographed on neutral Alumina (Woelm, act. grade III) by gradient elution with EtOAc/hexane to give the desired material as a syrup.

4,8-dimethyl-5-ethyl-1,3,3aα,4α,5,9bα-hexahydro-2-(N-methyl-pyrrolidin-2-ylethyl)-2H-pyrrolo[3,4-c]quinoline (xxix) (Compound 28 on Table I)

A cold solution of 75 ml of 0.94 M $BH_3$ THF was added dropwise to a cold solution of the above pyrrolo [3,4-c]quinoline (xxviii) in 50 ml of dry THF under $N_2$. The solution was stirred and refluxed under $N_2$ for 18 hours. Standard acid/$H_2O$ workup as described for similar compounds gave 0.8 g of a gold syrup that was converted to a dicitrate from an EtOAc solution of the syrup and 0.8 g of citric acid. A cream-colored solid was obtained, mp=140° (decomp).

EXAMPLE 10

(Method VI)

1,3-dioxo-3aα,4α,5,9bα-tetrahydro-2,4,8-trimethyl-2H-pyrrolo[3,4-c]quinoline (xxx)

A mixture of 13.7 g (0.057 mole) of (iii), 1.04 g (7.6 weight %) of $PtO_2$ and 250 ml of reagent grade MeOH was placed in a nickel-clad bottle on a Parr shaker. The reactor was charged with $H_2$ and shaken until $H_2$ uptake ceased. The catalyst was removed by filtration through a pad of celite. The pad was washed with 400 ml of acetone and combined with the MeOH filtrate. The combined filtrate was evaporated to dryness giving a peach-colored solid, mp 147°-148°.

5-benzoyl-1,3-dioxo-3aα,4α,5,9bα-tetrahydro-2,4,8-trimethyl-2H-pyrrolo[3,4-c]quinoline (xxxi)

Benzoyl chloride (1.14 g; 0.008 mole) in 25 ml of dry toluene was added in one portion to a mixture of 1.8 g (0.0074 mole) of (xxx), 0.82 g (0.008 mole) of triethylamine and 25 ml of dry toluene. The resultant mixture was stirred and refluxed for 5 hours and after cooling, it was diluted with 200 ml of EtOAc and transferred to a separatory funnel. The organic layer was washed with 100 ml of a saturated NaHCO$_3$ solution and H$_2$O and then dried (NaSO$_4$). Solvent removal in vacuo on a rotary evaporator gave a yellow-brown semisolid. Trituration with ether gave a cream-colored solid, mp 204°-205°.

5-benzyl-1,3,3aα,4α,5,9bα-hexahydro-2,4,8-trimethyl-2H-pyrrolo[3,4-c]quinoline (xxxii) (Compound 39 on Table I)

A solutin of BH$_3$.THF (55 ml of a 0.98 M solution) ws added under N$_2$ to a stirred solution of 1.8 g (0.0052 mole) of (xxxi) in 50 ml of dry THF. The mixture was refluxed for 18 hours under N$_2$, cooled and quenched with 30 ml of H$_2$O and 60 ml of 6 M HCl. The THF was distilled at atmospheric pressure and the remaining aqueous layer was made alkaline with 25 ml of 50% aqueous NaOH and then extracted with ether. The ether extract was dried (Na$_2$SO$_4$), evaporated to dryness on a rotary evaporator and the oil obtained was bulb-to-bulb distilled; bp 140°-145° at 0.25 mm Hg. Conversion to the citrate salt in ether gave a white solid, mp 88°-90°.

EXAMPLE 11

1,3,3aα,4α,5,9bα-hexahydro-2,4,8-trimethyl-2H-pyrrolo[3,4-c]quinoline (xxxiii) (Compound 40 on Table I)

To a solution of (xxx) (7.33 g; 0.03 mole) in 300 ml of dry THF was added gradually 9.1 g (0.225 mole) of lithium aluminum hydride under N$_2$ and the mixture was stirred and refluxed overnight.

The reaction flask was then chilled in an ice bath and the reaction quenched by adding a saturated aqueous Na$_2$SO$_4$ solution. Inorganic salts were filtered and the filtrate taken to dryness on a rotary evaporator to give a viscous brown oil. Bulb-to-bulb distillation yielded a pure product; bp 100°-110° at 0.35 mm Hg.

EXAMPLE 12

5-acetyl-1,3,3aα,4α,5,9bα-hexahydro-2,4,8-trimethyl-2H-pyrrolo[3,4-c]quinoline (xxxiv) (Compound 43 on Table I)

A solution of 1.5 g acetyl chloride in 20 ml of toluene was added dropwise to a rapidly stirred mixture of 2.6 g (0.012 mole) of (xxxiii), 100 ml toluene and 50 ml of 10% aqueous NaOH. The reaction mixture was stirred and heated at 45° under N$_2$ overnight.

The toluene layer was separated, combined with a toluene wash of the aqueous layer, backwashed with H$_2$O and dried (Na$_2$SO$_4$). The toluene solution was evaporated in vacuo and the residual oil distilled bulb-to-bulb; bp 110°-120° at 0.15 mm Hg. The oil was converted to a citrate salt in ether; mp 75°-80°.

EXAMPLE 13

A solution of 5.4 g of compound (va) in 100 ml of dry ether was vigorously stirred and treated dropwise with a solution of 8.91 g of di-p-toluoyl-l-tartaric acid in 200 ml of dry ether. Stirring was continued for 2½ hours. The white solid was filtered, washed with ether and dried.

The salt was dissolved in 2:1 ether/MeOH (300 ml) and allowed to stand at ambient temp. White crystals were filtered and washed with ether; yield 4.22 g. The filtrate was cooled in a refrigerator. An additional 0.65 g of crystals was collected; total yield, 4.87 g; $[\alpha]_D +45°$ (H$_2$O) C, 0.1.

The tartrate salt was dissolved in H$_2$O and made strongly alkaline with 10% NaOH soln. The free base was extracted into ether, washed with H$_2$O, dried (Na$_2$SO$_4$), and the ether removed in vacuo on a rotary evaporator; yield 2.15 g of colorless oil; $[\alpha]_D -86.63°$ (EtOH) C, 0.105.

The oil was converted to a citrate salt in the manner described above in Example 1; yield 2.8 g; $[\alpha]_D -38.75°$ (H$_2$O), C, 0.1.

The MeOH/ether filtrate from above was reduced to dryness. The residual salt was tritrated with EtOAc, ether, and dried; yield, 6.6 g; $[\alpha]_D +85°$, C, 0.1.

The salt was converted to its free base as described above to give 2.65 g of oil $[\alpha]_D +43.65°$ (EtOH), C, 0.12.

Conversion to the citrate salt as described above gave 3.25 g of solid; $[\alpha]_D +16.25°$ (H$_2$O) C, 0.1.

The compounds of this invention have been found to possess antipsychotic properties as evidenced by favorable comparisons with certain known antipsychotic drugs especially thioridazine and clozapine in standard experimental pharmacological and biochemical tests. For example, compounds of this invention antagonize apomorphine induced climbing in mice, antagonize α,4-dimethyl-3-hydroxyphenethylamine hydrochloride induced hyperactivity in rats, antagonize apomorphine induced hyperactivity more than apormorphine induced biting in rats, have very weak cataleptic effects in rats and antagonize the hyperactivity induced by injections of dopamine into the nucleus accumbens of rats. They also increase dopamine turnover in the limbic area of the rat brain as measured by the increase in homovanillic acid levels. These results indicate that the pyrrolo [3,4-c]quinolines of this invention would be antipsychotic agents which are relatively free of extrapyramidal side effects (EPS) and by implication would not induce tardive dyskinesia in human patients.

The antagonism of apomorphine induced climbing in mice as a test for antipsychotic drugs is described in Puech, et al., European Journal of Pharmacology, 50, 291-300 (1978); Costall, et al., European Journal of Pharmacology, 50, 39-50 (1978); Ther, et al. Arch. Int. Pharmacodyn., CXXXVIII, 302-310, (1962); and Vonvoightlander, et al. The Journal of Pharmacology and Experimental Therapeutics, 193, 88-94, (1975). The known clinically effective antipsychotic agents are able to antagonize climbing behavior in a dose dependent manner. When compared to the known antipsychotic compounds, materials of the invention compare favorably as seen by results summarized in the following Table II:

TABLE II

| Dose | Mean (of 10 mice) Highest Rung Climbed |
|---|---|
| — (vehicle) | 20.4 |
| 1.25 mg/kg i.p. of Thioridazine | 23.5 |
| 2.5  " | 15.1 |
| 5    " | 9.4 |
| 10   " | 3.7 |
| 20   " | 0 |
| — (vehicle) | 26.4 |
| 2.5 mg/kg i.p. of Clozapine | 24.3 |
| 5    " | 13.2 |
| 10   " | 8.4 |
| 20   " | 7.6 |
| — (vehicle) | 24.4 |
| 2.5 mg/kg i.p. of Compound (va) of the invention from Example 1 | 24.2 |
| 5 mg/kg i.p. of Compound (va) of the invention from Example 1 | 14.9 |
| 10 mg/kg i.p. of Compound (va) of the invention from Example 1 | 4.2 |
| 20 mg/kg i.p. of Compound (va) of the invention from Example 1 | 0.4 |

When tested for antipsychotic activity in the above mentioned tests in rats, compounds of the present invention demonstrate activity when administered interperitoneally at a dose from about 2.5 mg/kg body weight to 20 mg/kg body weight. A preferred compound of this invention of Formula (II) having a β-configuration wherein $R_2$, $R_4$ and $R_8$ are each methyl and $R_5$ is ethyl, demonstrated activity against apomorphine induced hyperactivity when administered interperitoneally at about 5 mg/kg body weight.

The present compounds also indicate effective analgesic-antiinflammatory activity in the standard inflamed rat paw test using carageenan as the irritant. The analgesic activity of the present compounds compares favorably with reference standards such as aspirin. Using the paw pressure test, a preferred compound of the invention of Formula (II) having a β-configuration wherein $R_2$, $R_4$ and $R_8$ are each methyl, and $R_5$ is ethyl increased the pain threshold by 73.2% at an oral dosage of 100 mg/kg body weight; in addition, this compound also exhibited significant antiinflammatory activity (74.1% decrease in foot volume) at this same dose. This result compares favorable with reference standards.

In general, products of the invention demonstrate analgesic activity in mice in laboratory tests when administered orally at a dose of from about 5 mg to 100 mg/kg body weight.

Analgesic activity has also been shown in compounds of the invention by the acetic acid-induced writhing test in mice, see R. Koster et al., "Acetic Acid for Analgesic Screening", Fed. Proc. 18:412 (1959). In this test, groups of six male Swiss-Webster mice (18-22 grams) are injected intraperitoneally with 10 ml/kg of 0.6% aqueous acetic acid 30 minutes after oral administration of test drug. The mice are then placed in a plexiglass chamber for observation, and the number of writhes for each animal is counted during a 10-minute period starting 3 minutes after acetic acid treatment. Comparison of the total number of writhes with the number observed for same-day placebo-treated control groups is used to determine activity of the test compound.

Antidepressant activity has also been shown for various compounds of the invention, e.g. compounds 11 and 28 from Table I. Suitable testing for antidepressant activity is the muricidal rat test in which it has been demonstrated that mouse-killing behavior by rats can be selectively antagonized by antidepressant drugs. All of the clinically effective antidepressants, e.g. tricyclics such as imipramine and amitriptyline, iprindole and mianserin, selectively antagonize muricidal behavior by rats. Reference works on this test are Z. P. Horovitz et al., Int. J. Neuropharmacol., 5:405-411 (1966) and J. B. Malick, Pharmacology Biochemistry and Behavior, 3:697-699 (1975).

In the muricide test, Long-Evans hooded rats, weighing 200-250 grams are isolated one per cage and maintained on ad lib food and water. The rats were tested for muricidal behavior by gently placing a male Swiss-Webster mouse in the front of the rat's home cage and observing whether it is killed during the 5-minute test session. Only rats that consistently kill mice within the 5-minute test period are used in this study. When utilized for drug testing, the rats are tested in the morning (same day control) and then given test drug or placebo intraperitoneally in the afternoon and retested for killing 30 and 60 minutes post drug. Immediately following the second mouse-killing test, all rats are tested for neurological impairment (ataxia) on a 45° inclined screen. As with the acetic acid writhing test, a comparison with placebo results determines activity of the test material.

When used as an antidepressant, compounds of the invention may be administered in an amount from about 5 to 100 mg/kg of body weight per day, preferably in a single administration at bedtime. Alternatively, the dosage could be equally divided and given 3 to 4 times per day. Projected usual doses for the treatment of clinical depression would be about 100 to 300 mg/day. In the muricidal rat test, imipramine, a known antidepressant would be effective at 10 mg/kg intraperitoneally and its usual range of daily dosage in man is between 75 and 300 mg in total.

In view of the indicated antipsychotic, antidepressant and analgesic activity of the present compounds, it is a further feature of the invention to provide a pharmaceutical composition which comprises, as active ingredient, an effective amount of a pyrrolo [3,4-c]quinoline or substituted pyrrolo [3,4-c]quinoline of Formulas (I) or (II) without the provisos (i) and (ii) described above for the compounds of Formula (I), in association with a non-toxic, pharmaceutically-acceptable diluent or carrier.

The pharmaceutical composition may be in a form suitable for various applications including oral, parenteral or rectal administration. For example, the composition may be formulated by means known to the art into tablets, capsules, aqueous or oily solutions, suspensions or emulsions, or sterile injectable aqueous or oily solutions or suspensions, dispersible powders or suppositories.

It will be recognized by those skilled in the present art that pharmaceutical compositions according to the invention may also contain, in addition to the active pyrrolo quinoline, one or more known drugs, such as an analgesic or antidepressant agent or any other suitable drug. For example, some of the compounds of the invention may induce a degree of emesis and it is contemplated that the compound may be administered concurrently with an anti-emetic drug.

Preferred pharmaceutical compositions of the invention include those suitable for oral administration in unit dosage form, for example, tablets and capsules which may contain between 1 and 600 mg of the active ingredient, or one suitable for intravenous, intramuscular or subcutaneous injection, for example, a sterile aqueous solution containing between 1 and 50 mg/ml of active ingredient utilized will be varied depending on, for example, the degree of activity of the pyrrolo quinoline involved.

The invention also contemplates a method for obtaining an antipsychotic, antidepressant or analgesic effect by administering to a host animal, such as man, in need of such treatment an effective amount of a pyrrolo [3,4-c]quinoline according to the invention.

Based on the activities which the present pyrrolo [3,4-c]quinolines demonstrate in the standard animal tests and a comparison of these with the activities of presently used antipsychotics and analgesics on these same tests, pharmaceutical compositions of the invention would, in general, be administered to humans to obtain antipsychotic or analgesic effects at an oral dose of between about 300 mg and 600 mg of active ingredient, an intramuscular or subcutaneous dose of between about 150 and 300 mg of active ingredient or an intravenous dose of between about 75 and 150 mg of active ingredient, the composition being administered 1 or 2 times per day. It will, however, be appreciated that the amount of pyrrolo [3,4-c]quinoline administered will vary depending on the particular compound which is used and the degree of treatment necessary.

The following examples are given to illustrate representative pharmaceutical compositions which are contemplated for use herein. While specific carriers and excipients are referred to in these examples, it will be appreciated that any of the well-known pharmaceutical carriers or additives can be used to prepare compositions according to the invention in acceptable dosage forms so as to provide a therapeutically effective amount of the active pyrrolo [3,4-c]quinoline to be administered.

EXAMPLE 14

This example illustrates the preparation of a tablet containing 100 mg of active ingredient:

| Formulation | Amounts (grams) |
| --- | --- |
| 5-ethyl-1,3,3aα,4α,5,9bα-hexahydro-2,4,8-trimethyl-2H-pyrrolo[3,4-c]quinoline (Compound (vb)) | 100 |
| Starch | 80 |
| Powdered Lactose | 80 |
| Talc | 20 |
| Total weight of Mix | 280 |

The above ingredients are combined, mixed and then compressed into slugs. The slugs may then be ground to form granules that will pass through a 14 to 16 mesh screen. The granules may then be recompressed into tablets using a suitable compression mold to form tablets, each weighing 280 mg. Other compounds of the invention may be formulated as pharmaceutical compositions in a similar manner.

EXAMPLE 15

Capsules containing 200 mg of Compound (vb) according to the invention may be prepared by uniformly mixing together the active compound and powdered lactose in a ratio of 200 mg active ingredient to 100 mg lactose. The resulting powder mix may then be packed into an appropriately sized gelatin capsule (No. 1).

EXAMPLE 16

An injectable composition suitable for intramuscular, intraperitoneal or subcutaneous injection may be prepared by mixing together 5.0 grams of a suitably soluble active compound, e.g. the citrate salt of Compound (vb) with the following:

| Chlorobutanol | 3.0 grams |
| --- | --- |
| Propylene Glycol | 20.0 ml |
| Water for Injection q.s | 1000.0 ml |

The resulting mixture is clarified by filtration and may then be placed into vials (containing 5 mg active compound) which are sealed and autoclaved.

It will be appreciated that various modifications may be made in the invention as defined in the following claims.

What is claimed is:

1. A compound selected from the group consisting of hexahydropyrrolo [3,4-c]quinolines of the following formula (I):

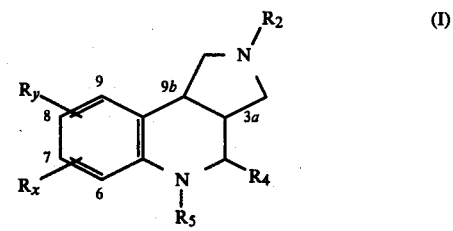

wherein
$R_2$ is

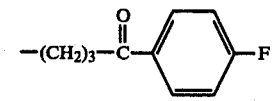

$R_4$ is hydrogen, $C_1$–$C_3$ alkyl or phenyl;
$R_5$ is hydrogen, $C_1$–$C_6$ alkyl, $C_3$–$C_6$ cycloalkyl, acetyl, benzyl or $CH_2CF_3$, and
$R_x$ and $R_y$, which may be the same or different, are hydrogen, halogen, trifluoromethyl, $C_1$–$C_6$ alkyl, $C_3$–$C_6$ cycloalkyl, $C_1$–$C_3$ alkoxy, $C_1$–$C_3$ alkylthio, hydroxy or cyano, or when $R_x$ and $R_y$ are alkoxy on adjacent carbons, they combine to form a 5-membered methylene dioxy or a 6-membered ethylene dioxy ring, and the pharmaceutically-acceptable acid addition salts thereof.

2. The compound of claim 1, wherein $R_x$ is hydrogen and $R_y$ is at the 8-position.

3. The compound of claim 2, wherein $R_y$ is selected from the group consisting of hydrogen, halogen, $C_1$–$C_6$ alkyl, $C_1$–$C_3$ alkoxy, hydroxy or cyano.

4. The compound of claim 1, wherein
$R_4$ is hydrogen or $C_1$–$C_3$ alkyl;
$R_5$ is $C_1$–$C_4$ alkyl;
$R_x$ is hydrogen; and
$R_y$ is at the 8-position and is $C_1$–$C_3$ alkyl, $C_3$–$C_6$ branched alkyl, $C_1$–$C_3$ alkoxy, halogen or hydroxy.

5. The compound of claim 1, wherein
$R_4$ is hydrogen, methyl, ethyl or phenyl;
$R_5$ is methyl, ethyl, normal propyl; or
$R_x$ is at the 7-position and is hydrogen or methyl; and $R_y$ is at the 8-position and is hydrogen, methyl, ethyl, iso-propyl, normal butyl or chloro.

6. The compound of claim 1, 2, 3, 4 or 5, wherein the hydrogens at positions 9*b*, 3*a* and 4 are cis to each other.

7. The compound of claim 1, wherein $R_4$ is methyl;
$R_5$ is ethyl;
$R_x$ is hydrogen; and
$R_y$ is at the 8-position and is methyl.

* * * * *